United States Patent [19]

Veeraraghavan

[11] Patent Number: 4,582,807
[45] Date of Patent: Apr. 15, 1986

[54] CULTIVATION MEDIUM FOR MYCOBACTERIA AND USE THEREOF

[76] Inventor: Natteri Veeraraghavan, Besant Nagar, Madras 600090, India

[21] Appl. No.: 403,827

[22] Filed: Jul. 30, 1982

[51] Int. Cl.$^4$ ............................ C12N 1/20; C12R 1/32
[52] U.S. Cl. ..................................... 435/253; 435/863
[58] Field of Search ................ 435/244, 253, 863, 866

[56] References Cited

U.S. PATENT DOCUMENTS

| | | | |
|---|---|---|---|
| 3,567,585 | 3/1971 | Bloch et al. | 435/866 |
| 3,983,003 | 9/1976 | Skinsnes et al. | 435/244 |
| 4,072,570 | 2/1978 | Williams | 435/866 |
| 4,205,126 | 6/1982 | Cartaya | 435/241 |

FOREIGN PATENT DOCUMENTS

| | | | |
|---|---|---|---|
| 0061793 | 5/1980 | Japan | 435/244 |
| 0071489 | 5/1980 | Japan | 435/253 |
| 0018588 | 2/1981 | Japan | 435/244 |
| 0908794 | 2/1982 | U.S.S.R. | 435/253 |

OTHER PUBLICATIONS

*Nutritional Requirements of Cultured Cells*, Katsuta, H. ed., Japan Scientific Societies Press, Tokyo, pp. 195-222 (1978).
Stanford, J. L. et al., *Int. Jour. of Leprosy*, vol. 45, No. 2 (1977), pp. 101-106, "A Study of Alleged Leprosy Bacillus Strain HI-75".
Ishaque, M. et al., *Int. Jour. of Leprosy*, vol. 45, No. 2 (1977), pp. 120-131, "Oxidation of Substrates by Host Grown *Mycobacterium leprae* and *Mycobacterium lepraemurium* and by in vitro Grown Mycobacteria Cultured from Human, Armadillo and Murine Lepromas".
Prabhakaran, K., *Lepr. Rev.*, vol. 44, pp. 112-119 (1973), "Dopa Metabolism by *Mycobacterium leprae*: Its Implications in Culture of the Bacillus and Chemotherapy of Leprosy".
Pattyn, S. R., *Bull. Wld. Hlth. Org.*, vol. 49, pp. 403-410 (1973), "The Problem of Cultivation of *Mycobacterium leprae*".
Olitizki, A. L., *The Lancet*, p. 196 (1977), "Cultivation of *Mycobacterium leprae*".
Kato, L., *Int. Jour. of Leprosy*, vol. 46, No. 2 (1978), "Cholesterol, A Factor Which is Required for Growth of Mycobacteria from Leprous Tissues".
Kato, L. et al., *Int. Jour. of Leprosy*, vol. 46, No. 4 (1978) pp. 376-385, "in vitro Cultivation of Mycobacteria in Cholesterol Lecithin Media from Lepromas of Rats Infected with *Mycobacterium lepraemurium*".

*Primary Examiner*—Thomas G. Wiseman
*Assistant Examiner*—Jean A. Heck
*Attorney, Agent, or Firm*—Ladas & Parry

[57] ABSTRACT

A medium for the rapid cultivation of mycobacteria, in particular leprosy and tubercle bacilli, comprises amino acids, sugars, phospholipids, muscle metabolism compounds, vitamins, inorganic salts and trace minerals.

12 Claims, No Drawings

CULTIVATION MEDIUM FOR MYCOBACTERIA AND USE THEREOF

BACKGROUND OF THE INVENTION

1. Field of the Invention

The present invention relates to the cultivation of mycobacteria and in particular leprosy bacilli and tubercle bacilli.

2. Description of the Prior Art

Leprosy is an ancient disease. There are over 12 million cases of leprosy in the world out of which about a fourth are present in India. No part of India is free from leprosy. The prevalence of the disease is high in southern and eastern States. The worst affected state is Tamil Nadu with approximately 800,000 patients. The other states where there are many sufferers are Andhra Pradesh, Binar and Orissa. In some districts 40 to 60 people out of every thousand suffer from leprosy.

About 25% of those having leprosy suffer from the infectious form of the disease.

Children are particularly susceptible to the disease. An assessment by the National Leprosy Control Programme has given an incidence rate of 42 per 1,000 in 8 school surveys in Tamil Nadu.

The causative organism of leprosy was discovered by Dr. Gerhard Henrik Armauer Hansen in 1873.

During the past 108 years scientists all over the world have been trying to grow the organism in the test tube but so far no one has succeded. Many claims have been made but none of them has been sustantiated.

Once the organism is grown in the test tube the whole outlook on this dreaded disease is bound to change since diagnosis will then become simple, rapid and reliable. At present, diagnosis depends on the examination of a smear of skin scraping. By the examination of the smear it is almost impossible to say whether the bacilli found are living or dead. To determine whether bacilli so obtained are living or dead mouse foot pads have to be inoculated and examined at periodical intervals. It takes almost a year before such examinations are conclusive.

However, if there were a suitable cultivation technique, the results could be obtained in a few days. If the organisms were found to be dead the treatment of the patient could be discontinued. This would be a great boon to the patient. Also, it may be possible to give a certificate to the patient that he is completely cured which is not possible now. This would be a great moral boost to the patient and a tremendous relief to his relatives.

Furthermore, once the organism is grown in a test tube drugs can be tested and the most suitable and effective of them can be prescribed for the patient.

With periodical examination of cultures grown from samples obtained from a patient it would be possible for the physican to follow the course of the disease in the patient and assess the value of the treatment given to him.

Only when the organism can be grown in the test tube can an anti-leprosy vaccine be prepared for preventing the disease among contacts of patients and for modifying the disease among those who are already infected.

Development of an anti-leprosy vaccine will be very useful in preventing or arresting the disease among children who are very susceptible to the infection. As Sir Leonard-Rogers pointed out if all children are kept free from infection for the first 10 years of their lives, leprosy would almost or entirely die out of an endemic country within two generations.

Even today we do not know exactly how the disease spreads in the community. If a simple method of growing the organism were available it would be possible to decide on the route of infection and take suitable measures to prevent the disease among the population.

Furthermore, satisfactory cultivation of leprosy bacilli would greatly facilitate the testing of new drugs against the disease.

It is now recognized that some of the strains of leprosy bacilli isolated from patients are resistant to certain drugs.

At present, testing for sensitivity is done in mice. The animals are given the drug regularly and after a course of treatment infected in the foot pad with leprosy bacillus. If multiplication of bacilli is prevented in the foot pad it means that the organism is sensitive to the drug and that it can be used for treatment. This evaluation takes about a year. This requires an air-conditioned room for keeping the mice under observation and enormous labour and expense in feeding and looking after the infected mice for long periods.

With a suitable cultivation technique all this can be circumvented. There is no need to handle mice at all. The experiments may be carried out in ordinary tissure culture tubes and the results obtained in 4 or 5 days.

The common anti-leprosy drugs can be tested against bacilli infecting a particular patient and those which kill the organism can be selected for the treatment. If the bacilli are resistant to any drug that drug is not used in treatment.

The culture medium routinely used for the isolation of tubercle bacilli from sputum and other infective materials from patients is the Lowenstein-Jensen medium. This is a complex medium which contains contents of hen's eggs as an important constitutent. It takes about a month for the colonies of tubercle bacilli to grow in the medium. Therefore, the patient has to wait for about a month for confirmation of the diagnosis. The drugs routinely used for treatment of tuberculosis are streptomycin, paraaminosalicylic acid, isoniazid, rifampicin, clofazamine and thiacetazone.

The sensitivity of the organism from each patient to each of the above group of drugs varies. Some strains may be resistant to certain drugs but not others. Therefore, it is essential to find out to which drug the organism is susceptible. and administer that singly or in combination.

For this purpose a simple and rapid method of testing for drug sensitivity is essential. At present the organism is grown in the Lowenstein-Jensen medium which takes about 28 days. It is then tested in Lowenstein-Jensen medium containing different concentrations of each of the drugs. This takes another 28 days. Therefore, the treatment of the patient is delayed for about 2 months.

SUMMARY OF THE INVENTION

It is accordingly an object of the present invention to provide a cultivation medium suitable for the growth of mycobacteria and in particular leprosy and tubercle bacilli.

It is a further object of the invention to provide a technique for the rapid cultivation of such bacilli.

Thus, the present invention provides a medium consisting essentially of acidic amino acids, aspartic acid and its amide asparagine and glutamic acid; the neutral amino acids β-alanine, DL-α alanine, phenylalanine, tyrosine, cystine, cysteine, proline, serine, leucine, and methionine; the basic amino acid arginine; compounds associated with muscle metabolism glycogen, glutathione, adenylic acid, creatine, sarcosine, carnatine, carnosine, glycocyamin, adenosine diphosphate, adenosine triphosphate, phosphocreatin; together with at least one monosaccharide sugar, at least one phospholipid, a pyramidine and cholesterol, linoleic acid, cleic acid, histamine, neparin, thyroxin, vitamins, dextran, protamine sulphate, inorganic salts and trace minerals.

Suitable monosaccharide sugars indicate glucosamine, mannose, arabinose, galactose and D-ribose. Suitable phospholipids include lecithin, phosphatidyl ethanolamine and phosphatidyl inositol. Suitable pyramidines include adenosine and cytosine.

The medium is free of protein.

Desirably, the pH of the medium is in the range 7.0 to 7.2.

DETAILED DESCRIPTION OF PREFERRED EMBODIMENTS

The medium of the present invention desirably has a total nitrogen content of from 1.0 to 1.25 mg/ml preferably 1.1 to 1.15 mg/ml typically about 1.12 mg/ml. The amino nitrogen content is desirably in the range 0.42 to 0.56 mg/ml preferably 0.46 to 0.52 typically about 0.49 mg/ml.

Typically, the medium of the present invention contains a total about 2 to 2.5 grams/liter of acidic amino acids conveniently the acids are present in a ratio of L-asparagine: L-glutamic acid of 4–6:4–6:1. Preferably there may be about 1 gram/liter L-aspartic acid, 1 gram/liter L-asparagine and 0.2 grams/liter L-glutamic acid.

Typically the medium of the present invention contains a total of about 3.5 to 4.1 g/liter of neutral amino acids conveniently such acids are present the following amounts:

β-alanine: 1.35–1.85 preferably 1.5 g/liter
DL-αalanine: 0.4–0.6 preferably 0.5 g/liter
L-proline: 0.08–0.12 preferably 0.1 g/liter
DL-serine: 0.08–0.12 preferably 0.1 g/liter
L-leucine: 0.08–0.12 preferably 0.1 g/liter
phenylalanine: 0.06–0.08 preferably 0.07 g/liter
methionine: 0.025–0.035 preferably 0.03 g/liter
cystine: 0.45–0.5 preferably 0.48 g/liter
tyrosine: 0.65–0.8 preferably 0.72 g/liter
cysteine: 0.15–0.25 preferably 0.2 g/liter Typically the medium of the present invention contains about 120–160 preferably about 140 mg/liter of arginine, for example as its hydrochloride salt.

Other amino acids such as L-glycine, γ-aminobutyric acid, taurine, glycylglycine, carnatine are also usefully present in a medium of the present invention in a total amount of up to about 1 g. per liter. When such acids are present, glycine, glycylglycine and carnatine (typically as its hydrochloride) will normally predominate and be present in roughly equal amounts.

The monosaccharide sugar content of the medium of the invention should be present in an amount of 1 to 1.5 grams per liter typically about 1.2 grams per liter. Normally over 95% by weight of the sugar will consist of glucosamine, galactose, and arabinose, typically in roughly equal amounts.

The phospholipid content of the medium is desirably about 5–10, preferably about 7.5 mg/liter. For example the medium can contain lecithin phosphatidyl ethanolamine and phosphatidyl inositol in substantially equal amounts as the phospholipid component.

The "muscle metabolism" compounds are normally present in a total amount of 350–420 mg/liter, typically about 385 mg/liter with a mixture of glycogen and glutathione in weight ratio of about 2:1 forming at least 75% of the total.

Adenosine and cytosine are typically present in a total amount of 40 to 50 mg/liter, for example about 40 mg. adenosine and 5 mg. cytosine.

Cholesterol is normally present in an amount of 5–15 mg. per liter, typically about 10 mg. per liter.

Linoleic acid is present in an amount of about 0.4 to 0.6 preferably about 0.5 mg/liter and oleic acid in an amount of 1–1.5 preferably about 1.25 mg/liter.

The histamine content, for example as the diphosphate is normally in the range 4 to 6 mg/liter and is typically about 5 mg/ml.

The heparin content is determined by the same parameters as the histamine.

Thyroxin is normally present in trace amounts, for example about 0.025 mg/liter.

The vitamins present in the medium include most of the B complex vitamins, (including, thiamine, riboflavin, nicotinic acid (niacin), nicotinamide, pyridoxine pyridoxal, pantothenic acid or a salt thereof, inositol, paraaminobenzoic acid, folic acid and biotin and vitamin $B_{12}$), vitamin C (ascorbic acid), vitamin $D_2$ (calciferol) and desirably trace amounts of vitamin E and vitamin K. Typically, the vitamin B compounds make up about 3.5–5 mg/liter, optimally about 4 mg per liter and the vitamin $D_2$ content is about 5 mg/liter and the vitamin C content about 10 mg/liter.

Dextran is typically present in an amount of about 4–6 g/liter, preferably about 5 g/liter.

Protamine sulfate is present as for 2–3 mg/liter, for example 2.5 mg/liter.

Suitable inorganic salts for incorporation in the medium include sodium chlorine, potassium chloride, calcium chloride, magnesium sulfate, sodium dihydrogen phosphate. Typically, such salts make up 6–10 g/liter of the medium, preferably about 7.5 to 8 g/liter.

Sodium citrate, zinc sulfate, copper sulfate, ferric ammonium citrate and manganese chloride are typical trace minerals for incorporation in the medium of the invention.

The composition can also usefully contain additional materials such as pimelic acid and the alpha epsilon diamino dervative thereof, sodium acetate and sodium succinate.

Conveniently, various stock solutions are prepared first prior to producing the medium of the invention. Usefully, these stock solutions are (1) a solution of the inorganic salts, (2) a solution of the trace minerals, (3) a solution comprising the amino acids (with the exception of tyrosine, cystine and cysteline), the "muscle metabolism" compounds and the sugars and (4) a solution of the "B" vitamins and vitamins E and K. All such stock solutions are formulated in highly sterile water, for example that which has been doubly distilled in glass vessels. Typically, the second and third of these stock solutions are combined before formulation of the medium of the invention.

Normally one proceeds by adding the first solution to highly sterilized water and follows this with solutions of cystine and tyrosine. The combination of the second and third stock solutions may then be added followed by glycerol and then the fourth stock solution. The remaining components are then added.

Generally the medium is prepared fresh by mixing the various sterile components. It can, however, be stored in a refrigerator for periods ranging from 2 to 4 weeks without any marked deterioration in its value. It can be filtered through a 0.22 nm membrane filter.

For isolation of leprosy bacillus from skin scrapings penicillin, streptomycin and mycostatin are added to the medium in a final concentration of 100 units, 100 mg and 30 units per ml respectively.

Once the organism is isolated in a pure culture, with good technique the addition of antibiotics can be dispensed with. However, even if streptomycin is omitted from the medium it may be useful to add 50 units of penicillin and 30 units of mycostatin per ml.

As a result of the use of this medium it is now possible to isolate leprosy bacillus from cases of lepromatous leprosy using the routine slit and scrape method of skin scraping. The selected area is swabbed with tincture of iodine and the iodine is completely removed by swabbing with a mixture of alcohol and ether. An ordinary safety razor is broken into 6 or 8 pieces. One of the pieces is picked up with an artery forceps and sterilized by dipping in the alcohol ether solution. It is flamed and when cooled with the sharp edge a cut 5 mm long and 0.5 mm deep is made through the dermis of the skin and the material scraped. The piece of blade with the scraped material is dropped into a 5 ml tissure culture tube containing 0.5 to 0.7 ml of chilled medium according to the invention. Four or 5 scrapings from different sites are made from each case and the blade pieces with the material are dropped into the medium. It is shaken well to disperse the material and the culture tube is transported on ice to the laboratory.

At the laboratory the culture is shaken well and transferred to a fresh tube discarding the pieces of blade.

For good results 1.5 ml of culture should be put into a 10 ml tissue culture tube (15×125 ml). Results are better if the culture tube is stoppered with a cork. Bakelite screw caps can also be used provided they fit well and close the mouth of the tube tightly.

When 5 ml tissue culture tubes (15×75 mm) are used the volume of the culture should be 0.5 to 0.7 ml.

It has been found that the organisms Leprosy bacilli grow well in the medium of the invention at 10° C. They continue to grow even at 0° C. although the rate is slower. But, there is no evidence of growth at −5° C. In the absence of a BOD incubator, the cultures can be incubated in the lowest shelf of an ordinary household refrigerator where the temperature ranges from 5° to 10° C. For storage, the cultures are shifted to the top shelf where the temperature ranges from 0° to 5° C.

Smears are made by mixing formal-milk solution with an equal volume of human serum, centrifuging the mixture at 3000 rpm for 15 min. and using the supernatant for making the smears. Either 0.005 or 0.01 ml of the culture is mixed with an equal volume of formal-milk-serum mixture and smears made on clean microscopic slides. They are dried under a 60 watt lamp and heat fixed on the lid of a boiling water bath for 2 min. They are then stained by the standard Ziehl-Neelson method.

In order to have reliable results it is necessary to count the number of bacilli in the whole smear. When the number of organisms is very large, appropriate dilution of the culture is made, smears prepared, and counted.

After several trials it was found that a fairly reliable method of assessing the increase in number is the following: single bacilli (SB), bacilli in groups of 2 to 10 (G), 10 to 20 (BG), and 20 and above (VBG) are counted separately and the increase in number in each category noted. An increase in the number of single bacilli (SE) and the group 2 to 10 (G) indicates evidence of multiplication.

For best results the dilution of the culture with medium of the invention should be such as to result in the optimum number of organisms required for growth. This varies with each strain.

The method adopted is to inoculate the culture, incubate it at 5° to 10° C. for one to two days depending on the initial count and then transfer it on to area 0° to 5° C. where it can be stored for months as long as it is not opened.

Subculture, if required, is done only after 2 to 3 weeks or longer. This period appears to be necessary for good growth.

In order to give the patient the best treatment it is necessary to know which of the common anti-leprosy drugs, dapsone, rifampicin, clofazimine, etc., are most effective against the organism. Using the method of growing the organism in culture with medium of the invention, a simple and elegant method has been standardized for testing the organsims sensitivity to different drugs. The details of the method are as follows:

The method of collection and transport of material from leprosy patients has been described earlier.

In the laboratory the culture containing the material and pieces of blades is shaken well. The culture is pipetted out and put into fresh 5 ml culture tubes discarding the blade pieces.

As the result of a systematic study, it has been found that the optimum final concentrations of dapsone, rifampicin, and clofazimine that should be used for testing the sensitivity of leprosy bacillus isolated are 0.01, 0.001, and 0.01 mg/ml respectively.

At the outset a smear is made of the culture containing the material from 4 or 5 scrapings in order to have a rough idea of the number of organisms present in 0.005 ml.

If this number is substantial testing for drug sensitivity can be undertaken straight away. If, however, the number of bacilli is small, the organisms have to be multiplied before the test can be undertaken.

When the count is high, the culture is diluted with an appropriate volume of the medium of the invention to give a concentration of about 100 to 200 bacilli in the whole smear prepared from 0.005 ml of culture.

The diluted culture is shaken well and 0.475 ml pipetted out each time and delivered into a 5 ml culture tube. Four cultures are prepared. To the first tube dapsone is added, to the second rifampicin and to the third clofazamine. To the fourth tube no drug is added and it serves as a control. The final concentrations of dapsone rifampicin and clofazamine are 0.01, 0.001, 0.01 mg/ml respectively.

A smear is made of the control tube and the cultures are incubated at 7° to 10° C. Smears are made on the third day and the number of organisms in 0.005 ml of the first, second and third cultures is compared with that in the control culture.

A comparison of the counts in the control culture before and after incubation would indicate whether the bacilli are alive and are multiplying.

If the count in the cultures treated with the drugs shows a 50% reduction or more the organism is considered sensitive to the drug.

The procedure for testing new drugs is exactly the same as that described for testing the sensitivity of strains isolated from leprosy patients. In this case a known strain of leprosy bacillus isolated from an untreated case of leprosy is used. The drug is added on various dilutions to the culture. Smears are made before the addition of the drug and 5 days after incubation. The inhibition of growth, if any, caused by the drug and the particular dilution in which it is caused are noted.

The method is so simple that screening of new drugs become easy and quick. The results can be obtained in 3 or 4 days compared with about 1 year in the mouse test.

It has not been possible hitherto to produce an antileprosy vaccine for the simple reason that the organism has not been cultivated in cultures in the test tube.

The World Health Organization has embarked on a big programme to multiply the bacillin in armadillos, separate the bacilli from the tissues and use it as a vaccine.

But these animals are scarce and are found mainly in the southern part of the U.S.A. They do not breed readily in captivity. The incubation period of the disease in them is variable and long, sometimes as long as two years and the yield of bacilli limited.

It is unrealistic to expect that enough vaccine can be prepared from this source to treat even a small fraction of the world's leprosy suffering. Even if it were possible the cost would be prohibitive.

On the other hand with a culture technique, organism isolated from the patient can be grown and made into a vaccine and administered to him.

The medium of the invention is also of use in the cultivation of tubercle bacilli.

The method of testing is exactly similar to that described for leprosy bacillus except for the fact that cultures are incubated at 37° C. The antibiotics routinely tested are isoniazid, streptomycin, paraaminosalicylic acid, cycloserine, ethionamide and rifampicin.

The medium of the invention has the advantage over the traditional Lowenstein-Jensen medium in that it is completely synthetic. It can be prepared easily and has the further advantage that when living bacilli are present in the sputum and other discharges they start multiplying rapidly and good growth can be obtained in 2 to 3 days. This will be of great advantage in the diagnosis of the disease which at present can take up to 2 months.

The production and use of the medium of the invention will now be exemplified.

PRODUCTION OF THE MEDIUM

In order to save time the following stock solutions are prepared, tested for sterility and stored in a refrigerator. They are used whenever required.

STOCK SOLUTION 1

Sodium chloride: 6.8 g
Potassium chloride: 0.4 g
Calcium chloride: 0.2 g
Magnesium sulphate: 0.2 g
Sodium dihydrogen phosphate: 0.14 g
Double glass distilled water: 100 ml
(Only Analytical Reagent grade chemicals should be used).

STOCK SOLUTION 2

Sodium citrate: 200 mg
Zinc sulphate: 1 mg
Copper sulphate: 1 mg
Ferric ammonium citrate: 10 mg
Manganese chloride: 1 mg
Stock solutions 1 and 2 are sterilized by autoclaving at 10 pounds for 10 minutes.

STOCK SOLUTION 3

L-aspartic acid: 500 mg
L-asparagine: 500 mg
L-glutamic acid: 100 mg
B-alanine: 750 mg
DL-a-alanine: 250 mg
L-glycine: 100 mg
L-proline: 50 mg
DL-serine: 50 mg
L-leucine: 50 mg
DL-phenylalanine: 35 mg
L-methionine: 15 mg
L-arginine hydrochloride: 70 mg
r-aminobutyric acid: 50 mg
Taurine: 50 mg
Glycylglycine: 100 mg
Carnatine hydrochloride: 100 mg
Carnosine: 100 mg
Sarcosine: 100 mg
Glycogen: 100 mg
Glutathione: 50 mg
Glycocyamine: 50 mg
Adenylic acid: 10 mg
Adenosine diphosphate: 10 mg
Adenosine triphosphate: 10 mg
Phosphocreatin: 10 mg
Cytosine: 25 mg
Alpha epsilon diaminopimelic acid: 10 mg
Pimelic acid: 10 mg
D (+) Glucosamine: 200 mg
D-galactose: 200 mg
D(−) arabinose: 200 mg
D-ribose: 10 mg
Sodium acetate: 100 mg
Sodium succinate: 100 mg
Magnesium sulphate: 500 mg
Stock solution 2: 0.5 ml
Double glass distilled water: 50 ml
Sterilized by filtration in 0.22 n membrane filter.

STOCK SOLUTION 4

Thiamine hydrochloride (Vitamin $B_1$): 10 mg
Nicotinic acid (a B complex vitamin): 10 mg
Nicotinamide (a B complex vitamin): 10 mg
Pyridoxine hydrochloride (a B complex vitamin): 10 mg
Pyridoxal chloride (a B complex vitamin): 10 mg
Calcium pantothenate (a B complex vitamin): 20 mg
Inositol (a B complex vitamin): 20 mg
Paraaminobenzoic acid (a B complex vitamin): 10 mg
Folic acid (a B complex vitamin): 5 mg
Riboflavin (Vitamin $B_2$): 1 mg
Biotin crystalline (a B complex vitamin): 1 mg
Vitamin $B_{12}$: 200 $\mu$g
Vitamin K: 25 $\mu$g
Vitamin E: 25 $\mu$g
Double glass distilled water: 25 ml
Sterilized by filtration through a 0.22 n membrane filter.

PREPARATION OF THE MEDIUM V

The medium is actually prepared as follows:
Double glass distilled water: 49.625 ml
Stock solution 1: 10.00 ml
Cystine (24 mg/ml): 2.00 ml
Tyrosine (36 mg/ml): 2.00 ml
Stock solution 3: 10.00 ml
Glycerol (Analar): 1.00 ml
Stock solution 4: 1.00 ml
Cysteine hydrochloride (10 mg/ml): 2.00 ml
Adenosine (5 mg/ml): 8.00 ml
Phosphotidyl ethanolamine (1 mg/ml): 0.25 ml
Phosphotidyl inositol (1 mg/ml): 0.25 ml
Phosphocreatin (1 mg/ml): 0.50 ml
Calciferol (Vitamin $D_2$) (1 mg/ml): 0.50 ml
Cholesterol (2 mg/ml): 0.50 ml
Linoleic acid (0.1 mg/ml): 0.50 ml
Oleic acid (1 mg/ml): 0.125 ml
Histamine diphosphate (1 mg/ml): 0.50 ml
Heparin (1 mg/ml): 0.50 ml
Tween 80 (2.5%: optional): 2.00 ml
Cardiolipin (0.03%): 0.125 ml
Lecithin (0.2%): 0.125 ml
Creatine (5 mg/ml): 1.00 ml
Ascorbic acid (Vitamin C) (1 mg/ml): 1.00 ml
L-thyroxine (0.01 mg/ml): 0.25 ml
Dextran (100 mg/ml): 5.00 ml
Protamine sulphate (0.1 mg/ml): 2.50 ml
Mucin (1 mg/ml): 2.00 ml
pH of the medium is adjusted to 7.0–7.2. The medium prepared by adding each of the ingredients, which have been tested for sterility, in the order given.

The final medium without the addition of antibiotics is tested for sterility and used.

TESTING FOR THE SENSITIVITY OF ISOLATES

The following is an example of testing a strain of leprosy bacillus isolated from a patient for drug sensitivity.

The strain was isolated from a lepromatous patient having reaction. The strain was isolated in culture in medium V.

The organism isolated from the patient was mixed with the medium V to give a suitable count of about 100 to 200 bacilli in 0.005 ml.

It was added in 0.475 ml quantities to 4 culture tubes. To the fourth tube 0.5 ml was added. To the first tube was added 0.025 ml of a dapsone solution to give a final concentration of 0.01 mg/ml. To the second tube 0.025 ml of rifampicin was added to give a final concentration of 0.001 mg/ml. To the third tube was added 0.025 ml of clofazamine to give a final concentration of 0.01 mg/ml. No drug was added to the fourth tube which served as a control.

Smears were made at the start of the experiment and after 3 days incubation at 7° C. The smears were stained and the number of bacilli in each smear counted. The results are given below:

| Starch | Nature of Drug | Final conc. mg/ml | Counts in Culture 0 hr | | | | Counts in Culture 3 days | | | | Percentage of inhibition | | | |
|---|---|---|---|---|---|---|---|---|---|---|---|---|---|---|
| | | | VBG | BG | G | SB | VBG | BG | G | SB | BVG | BG | G | SB |
| C 47 | Dapsone | 0.01 | | | | | 0 | 0 | 157 | 78 | | | 84 | 85 |
| | Rif. | 0.001 | | | | | 0 | 0 | 209 | 118 | | | 78 | 77 |
| | Clof. | 0.01 | | | | | 0 | 0 | 144 | 86 | | | 78 | 75 |
| | — | — | 0 | 0 | 236 | 157 | 0 | 0 | 964 | 520 | | | | |
| Multiplication factor | | | | | | | | | 3.6 | 3.3 | | | | |

It will be seen that there was more than 3.3-fold multiplication of the bacilli in the culture to which no drug was added.

On the other hand, the first culture to which dapsone was added showed 84% inhibition while the second and third cultures to which rifampicin and clofazamine were added showed about 77% inhibition.

This indicates that the patient's leprosy bacilli are sensitive to dapsone, rifampicin and clofazamine and that any of the drugs singly or in combination can be used in his treatment.

TESTING OF NEW DRUGS

Two drugs commonly used for the treatment of tuberculosis namely isonicotinic acid hydraside (INH) and thiacetasone (Thia) were tested to determine whether they had any action on the leprosy bacillus.

The strain C 42 isolated from an untreated case of lepromatous leprosy was used to test the action of the two drugs. Dapsone was included as a control. The procedure followed was exactly similar to that adopted for testing the sensitivity to drugs of strain C 47 from a patient showing reaction.

| Strain | Nature of drug | Final conc. mg/ml | Counts in culture at 0 hr | | | | 3 days | | | | | | | |
|---|---|---|---|---|---|---|---|---|---|---|---|---|---|---|
| | | | VBG | BG | G | SB | VBG | BG | G | SB | VBG | BG | G | SB |
| C 42 | DAPSONE | 0.01 | | | | | 0 | 2 | 88 | 76 | | | 93 | 94 |
| | INH | 0.01 | | | | | 0 | 0 | 765 | 355 | | | 42 | 36 |
| | Thia | 0.01 | | | | | 0 | 1 | 390 | 235 | | | 70 | 58 |
| | — | — | 0 | 1 | 236 | 178 | 1 | 1 | 1321 | 553 | | | | |
| Multiplication factor | | | | | | | | | 5 | 3 | | | | |

It will be seen that there was more than three-fold multiplication in the control culture to which no drug was added.

The inhibition produced by dapsone on this strain was excellent, above 93%: that produced by nicotinic acid hydrazi was below 50%. On the other hand, thiacetazone produced an appreciable degree of inhibition.

Based on these results it is concluded that the best drug to use against this strain is dapsone.

I claim:

1. A medium suitable for the cultivation of mycobacteria consisting essentially of
   (a) from 2 to 2.5 grams per liter of an acidic amino acid selected from the group consisting of aspartic acid, asparagine, glutamic acid and mixtures thereof
   (b) a total of 3.4 to 4.1 grams per liter of neutral amino acid selected from the group consisting of β-alanine, DL-α alanine, phenylalanine, tyrosine, cystine, cysteine, proline, serine, leucine methionine and mixtures thereof
   (c) 120–160 mg per liter of arginine
   (d) a total of 350–420 mg per liter of "muscle metabolism compound" selected from the group consisting of glycogen, glutathione, adenylic acid, creatine, sarcosine, carnatine, carnosine, glycocyamine, adenosine diphosphate, adenosine triphosphate, phosphocreatin and mixtures thereof
   (e) a total of from 1 to 1.5 grams/liter of monosaccharaide sugar selected from the group consisting of glucosamine, mannose, arabinose, galactose, D-ribose and mixtures thereof
   (f) from 40–50 mg/liter of adenosine, cytosine or a mixture of the two
   (g) a total of from 5 to 10 mg/liter of phospholipid selected from the group consisting of lecithin, phosphotidyl ethanolamine, phosphotidyl inositol, and mixtures thereof
   (h) 5–15 mg/liter cholesterol
   (i) 0.4–0.6 mg/liter linoleic acid
   (j) 1–1.5 mg/liter oleic acid
   (k) 4–6 mg/liter histamine
   (l) 4–6 mg/liter heparin
   (m) a total of 3.5–5 mg/liter of a vitamin selected from the group consisting of vitamins B, D, E, K and mixtures thereof
   (n) 4–6 g/liter dextran
   (o) 2–3 mg/liter protamine sulfate
   (p) 6–10 g/liter inorganic salts and
   (q) trace minerals
   in sterile water.

2. A medium according to claim 1, wherein the pH is in the range 7.2–7.4.

3. A medium according to claim 1, wherein the acidic amino acids are present in a ratio 4–6:4–6:1 of L-aspartic acid: asparagine: L-glutamic acid.

4. A medium according to claim 1, wherein the amounts of neutral amino acids present are:
   β-alanine: 1.35–1.85 g/liter
   DL-α alanine: 0.4–0.6 g/liter
   L-proline: 0.08–0.12 g/liter
   DL-serine: 0.08–0.12 g/liter
   L-leucine: 0.08–0.12 g/liter
   phenyl alanine: 0.06–0.08 g/liter
   methionine: 0.025–0.035 g/liter
   cystine: 0.45–0.5 g/liter
   tyrosine: 0.65–0.8 g/liter
   cysteine: 0.15–0.25 g/liter.

5. A medium according to any one of claims 1, 2, 3 or 4, which further contains an amino acid selected from the group consisting of L-glycine, γ-aminobutyric acid, taurine, glycylglycine carnatine and mixtures thereof.

6. A medium according to claims 1, 2, 3 or 4, wherein 95–100% by weight of the said monosaccharide sugar component consists of glucosamine, galactose and arabinose each one of said sugars being present in a substantially equal amount by weight.

7. A medium according to claims 1, 2, 3 or 4, wherein 75–100% of the "muscle metabolism compounds" is a mixture of glycogen and glutathione in a substantially 2:1 weight ratio.

8. A method for cultivating leprosy bacilli which comprises introducing said bacilli into a medium consisting essentially of
   (a) from 2 to 2.5 grams per liter of an acidic amino acid selected from the group consisting of aspartic acid, asparagine, glutamic acid and mixtures thereof
   (b) a total of 3.5 to 4.1 grams per liter of neutral amino acid selected from the group consisting of β-alanine, DL-α alanine, pheylalanine, tyrosine, cystine, cysteine, proline, serine, leucine methionine and mixtures thereof
   (c) 120–160 mg/per liter of arginine
   (d) a total of from 350–420 mg per liter of "muscle metabolism compound" selected from the group consisting of glycogen, glutathione, adenylic acid, creatine, sarcosine, carnatine, carnosine, glycocyamine, adenosine diphosphate, adenosine triphosphate, phosphocreatin and mixtures thereof
   (e) a total of from 1 to 1.5 grams liter of monosaccharide sugar selected from the group consisting of glucosamine, mannose, arabinose, galactose, D-ribose and mixtures thereof
   (f) from 40–50 mg/liter of adenosine, cytosine or a mixture of the two
   (g) a total of 5 to 10 mg/liter of phospholipid selected from the group consisting of lecithin, phosphotidyl ethanolamine, phosphotidyl inositol, and mixtures thereof
   (h) 5–15 mg/liter cholesterol
   (i) 0.4–0.6 mg/liter linoleic acid
   (j) 1–1.5 mg/liter oleic acid
   (k) 4–6 mg/liter histamine
   (l) 4–6 mg/liter heparin
   (m) a total of 3.5–5 mg/liter of a vitamin selected from the group consisting of vitamins B, D, E, K and mixtures thereof
   (n) 4–6 g/liter dextran
   (o) 2–3 mg/liter protamine sulfate
   (p) 6–10 g/liter inorganic salts and
   (q) trace minerals
   in sterile water and maintaining said medium at a temperature of 0°–10° C.

9. A method for diagnosis leprosy which comprises placing skin scrapings from suspected leper in a medium consisting essentially of
   (a) from 2 to 2.5 grams per liter of an acidic amino acid selected from the group consisting of aspartic acid, asparagine glutamic acid and mixtures thereof
   (b) a total of from 3.5 to 4.1 grams per liter of neutral amino acid selected from the group consisting of β-alanine, DL-α alanine, phenylanine, tyrosine, cystine, cysteine, proline, serine, leucine methionine and mixtures thereof
   (c) 120–160 mg per liter of arginine
   (d) a total of from 350–420 mg per liter of "muscle metabolism compound" selected from the group consisting of glycogen, glutathione, adenylic acid, creatine, sarcosine, carnatine, carnosine, glycocyamine, adenosine diphosphate, adenosine triphosphate, phosphocreatin and mixtures thereof
   (e) a total of from 1 to 1.5 grams/liter of monosaccharide sugar selected from the group consisting of glucosamine, mannose, arabinose, galactose, D-ribose and mixtures thereof
(f) from 40-50 mg/liter of adenosine, cytosine or a mixture of the two
(g) a total of from 5 to 10 mg/liter of phospholipid selected from the group consisting of lecithin, phosphotidyl ethanolamine, phosphotidyl inositol and mixtures thereof
(h) 5-15 mg/liter cholesterol
(i) 0.4-0.6 mg/liter linoleic acid
(j) 1-1.5 mg/liter oleic acid
(k) 4-6 mg/liter histamine
(l) 4-6 mg/liter heparin
(m) a total of 3.5-5 mg/liter of a vitamin selected from the group consisting of vitamins B, D, E, K and mixtures thereof
(n) 4-6 g/liter dextran
(o) 2-3 mg/liter protamine sulfate
(p) 6-10 g/liter inorganic salts and
(q) trace minerals in sterile water and thereafter cultivating the scrpaings in said medium at 0°-10° C. and periodically determining by staining followed by visual observation whether the number of single bacilli present is increasing.

10. A method for testing the sensitivity of leprosy bacillus to a particular drug which comprises cultivating leprosy bacillus in a medium consisting essentially of
(a) from 2 to 2.5 grams per liter of an acidic amino acid selected from the group consisting of aspartic acid, asparagine, glutamic acid and mixtures thereof
(b) a total of from 3.5 to 4.1 grams per liter of neutral amino acid selected from the group consisting of β-alanine, DL-α alanine, phenylalanine, tyrosine, cystine, cysteine, proline, serine, leucine methionine and mixtures thereof
(c) 120-160 mg per liter of arginine
(d) a total of from 350-420 mg per liter of "muscle metabolism compound" selected from the group consisting of glycogen, glutathione, adenylic acid, creatine, sarcosine, carnatine, carnosine, glycocyamine, adenosine diphosphate, adenosine triphosphate, phosphocreatin and mixtures thereof
(e) a total of from 1 to 1.5 grams/liter of monosaccharide sugar selected from the group consisting of glucosamine, mannose, arabinose, galactose, D-ribose and mixtures thereof
(f) from 40-50 mg/liter of adenosine, cytosine or a mixture of the two
(g) a total of from 5 to 10 mg/liter of phospholipid selected from the group consisting of lecithin, phospotidyl ethanolamine, phosphotidyl inositol, and mixtures thereof
(h) 5-15 mg/liter cholesterol
(i) 0.4-0.6 mg/liter linoleic acid
(j) 1-15 mg/liter oleic acid
(k) 4-6 mg/liter histamine
(l) 4-6 mg/liter heparin
(m) a total of 3.5-5 mg/liter vitamin selected from the group consisting of vitamins B, D, E, K and mixtures thereof
(n) 4-6 g/liter dextran
(o) 2-3 mg/liter portamine sulfate
(p) 6-10 g/liter inorganic salts and
(q) trace minerals in sterile water in the presence of the test drug and determining by staining followed by visual observation whether the number of single bacilli present is increasing.

11. A method for diagnosing tuberculosis which comprises cultivating a specimen from one suspected of being tubercular in a medium consisting essentially of
(a) from 2 to 2.5 grams per liter of an acidic amino acid selected from the group consisting of aspartic acid, asparagine, glutamic acid and mixtures thereof
(b) a total of from 3.5 to 4.1 grams per liter of neutral amino acid selected from the group consisting of β-alanine, DL-α alanine, phenylalanine tyrosine, cystine, cysteine, proline, serine, leucine methionine and mixtures thereof
(c) 120-160 mg per liter of arginine
(d) a total of from 350-420 mg per liter of "muscle metabolism compound" selected from the group consisting of glycogen, glutathione, adenylic acid, creatine, sarcosine, carnatine, carnosine, glycocyamine, adenosine diphosphate, adenosine triphosphate, phosphocreatin and mixtures thereof
(e) a total of from 1 to 1.5 grams/liter of monosaccharide sugar selected from the group consisting of glucosamine, mannose, arabinose, galactose, D-ribose and mixtures thereof
(f) from 40-50 mg/liter of adenosine, cytosine or a mixture of the two
(g) a total of from 5 to 10 mg/liter of phospholipid selected from the group consisting of lecithin, phosphotidyl ethanolamine, phosphotidyl inositol and mixtures thereof
(h) 5-15 mg/liter cholesterol
(i) 0.4-0.6 mg/liter linoleic acid
(j) 1-1.5 mg/liter oleic acid
(k) 4-6 mg/liter histamine
(l) 4-6 mg/liter heparin
(m) a total of 3.5-5 mg/liter of a vitamin selected from the group consisting of vitamins B, D, E, K and mixtures thereof
(n) 406 g/liter dextran
(o) 2-3 mg/liter protamine sulfate
(p) 6-10 g/liter inorganic salts and
(q) trace minerals in sterile water at about 37° C. and periodically determining by staining followed by visual observation whether the number of tubercule bacilli present has increased.

12. A method for testing the sensitivty of tubercule bacilli to a particular drug which comprises cultivating tubercule bacilli in a medium consisting essentially of
(a) from 2 to 2.5 grams per liter of an acidic amino acid selected from the group consisting of aspartic acid, asparagine glutamic acid and mixtures thereof
(b) a total of from 3.5 to 4.1 grams per liter of neutral amino acid selected from the group consisting of β-alanine, DL-α alanine, phenylalanine, tyrosine, crystine, cysteine, proline, serine, leucine methionine and mixtures thereof
(c) 120-160 mg per liter of arginine
(d) a total of from 350-420 mg per liter of "muscle metabolism compound" selected from the group consisting of glycogen, glutathione, adenylic acid, creatine, sarcosine, carnatine, carnosine, glycocyamine, adenosine diphosphate, adenosine triphosphate phosphocreatin and mixtures thereof
(e) a total of from 1 to 1.5 grams/liter of monosaccharide sugar selected from the group consisting of glucosamine, mannose arabinose, galactose, D-ribose and mixtures thereof
(f) from 40–50 mg/liter of adenosine, cytosine or a mixture of the two
(g) a total of from 5 to 10 mg/liter of phospholipid selected from the group consisting of lecithin, phosphotidyl ethanolamine, phosphotidyl inositol, and mixtures thereof
(h) 5–15 mg/liter cholesterol
(i) 0.4–0.6 mg/liter linoleic acid
(j) 1–1.5 mg/liter oleic acid
(k) 4–6 mg/liter histamine
(l) 4–6 mg/liter heparin
(m) 3.5–5 mg/liter of a vitamin selected from the group consisting of vitamins B, D, E, K and mixtures thereof
(n) 4–6 g/liter dextran
(o) 2–3 mg/liter protamine sulfate
(p) 6–10 g/liter inorganic salts and
(q) trace minerals in sterile water in the presence of the test drug and periodically determining by staining followed by visual observation whether the number of tubercle bacilli present has increased.

* * * * *